United States Patent
Clarke et al.

(10) Patent No.: US 10,702,580 B2
(45) Date of Patent: Jul. 7, 2020

(54) BETA-CASEIN A2 AND ANTIOXIDANT CAPACITY

(71) Applicant: THE A2 MILK COMPANY LIMITED, Auckland (NZ)

(72) Inventors: Andrew John Clarke, Auckland (NZ); Malav Suchin Trivedi, Hollywood, FL (US)

(73) Assignee: THE A2 MILK COMPANY LIMITED, Auckland (NZ)

(*) Notice: Subject to any disclaimer, the term of this patent is extended or adjusted under 35 U.S.C. 154(b) by 0 days.

(21) Appl. No.: 15/576,012

(22) PCT Filed: May 20, 2016

(86) PCT No.: PCT/NZ2016/050081
§ 371 (c)(1),
(2) Date: Nov. 21, 2017

(87) PCT Pub. No.: WO2016/190750
PCT Pub. Date: Dec. 1, 2016

(65) Prior Publication Data
US 2018/0169186 A1    Jun. 21, 2018

Related U.S. Application Data (60) Provisional application No. 62/165,854, filed on May 22, 2015.

(51) Int. Cl.
| A61K 35/20 | (2006.01) |
| A61K 38/17 | (2006.01) |
| A23L 33/19 | (2016.01) |
| A23C 9/152 | (2006.01) |

(52) U.S. Cl.
CPC ........ *A61K 38/1709* (2013.01); *A23C 9/1526* (2013.01); *A23L 33/19* (2016.08); *A61K 35/20* (2013.01); *A23V 2002/00* (2013.01)

(58) Field of Classification Search
CPC .. A61K 38/1709; A61K 35/20; A23C 9/1526; A23L 33/19; A23V 2002/00
See application file for complete search history.

(56) References Cited

U.S. PATENT DOCUMENTS

| 2006/0280802 A1* | 12/2006 | Campbell | A61K 38/1709 424/535 |
| 2012/0157372 A1* | 6/2012 | Friel | C07K 4/12 514/2.3 |

FOREIGN PATENT DOCUMENTS

| WO | WO-1996/014577 A1 | 5/1996 |
| WO | WO-1996/036239 A1 | 11/1996 |
| WO | WO-2002/19832 A1 | 3/2002 |
| WO | WO-2014/193248 A1 | 12/2014 |
| WO | WO-2014/194292 A1 | 12/2014 |
| WO | WO-2015/005804 A1 | 1/2015 |
| WO | WO-2015/026245 A1 | 2/2015 |

OTHER PUBLICATIONS

Maritim et al, J Biochem Molecular Toxicology, vol. 17, No. 1, pp. 24-38. (Year: 2003).*
Martin et al, The FASEB Journal, vol. 23, pp. 3263-3272 (Year: 2009).*
Pal et al, Nutrients, 7, 7285-7297 (Year: 2015).*
Bell et al., Health implications of Milk containing β-casein with an A2 Genetic Variant, Critical reviews in Food Science and Nutrition, 46(1):93-100 (2006).
ClinicalTrials.gov, NCT02406469, Effects Comparison of A1 and A2 Milk on Gastrointestinal Physiology, Symptoms and Cognitive Behavior, Apr. 2, 2015.
Petrat-Melin et al., In vitro digestion of purified β-casein variants A1, A2, B and I: Effects on antioxidance and angiotensin-conversing enzyme inhibitory capacity, J. Dairy Sci, 98(1):15-26 (2015).
International Preliminary Report on Patentability, Australian Patent Office, PCT/NZ2016/050081, dated Nov. 28, 2017.
International Search Report and Written Opinion of the International Search Authority, Australian Patent Office, PCT/NZ2016/050081, dated Aug. 15, 2016.

* cited by examiner

*Primary Examiner* — Sudhakar Katakam
(74) *Attorney, Agent, or Firm* — Marshall, Gerstein & Borun LLP (57) ABSTRACT

Improving the antioxidant capacity in an animal by increasing the level of glutathione in the blood or tissue of the animal comprising providing a composition containing beta-casein to the animal for consumption, where the beta-casein comprises at least 75% by weight of one or more beta-caseins not capable of producing beta-casomorphin-7 on enzymatic digestion. Uses include as an oxidant, for treating or preventing the symptoms of cancer, inflammation, kwashiorkor (protein deficiency), seizure, autism, Down's syndrome, chronic fatigue syndrome, Alzheimer's disease, Parkinson's disease, sickle cell anaemia, liver disease, cystic fibrosis, HIV, AIDS, infection, heart attack, stroke, and diabetes, avoiding or reducing the effects of aging, promoting the recovery of tissue following physical exercise, and promoting fertility.

15 Claims, 5 Drawing Sheets

BETA-CASEIN A2 AND ANTIOXIDANT CAPACITY

CROSS-REFERENCE TO RELATED APPLICATIONS

This application is a national phase of International Patent Application No. PCT/NZ2016/050081, filed May 20, 2016, which claims the benefit of U.S. Provisional Application 62/165,854, filed May 22, 2015.

TECHNICAL FIELD

The invention relates to the milk protein A2 beta-casein and improving the antioxidant capacity in an animal by increasing the levels of glutathione in the body of the animal. In particular, the invention relates to milk and milk derived food products. The applicant has found that the consumption of milk and milk products that contain high levels of the A2 variant of the protein beta-casein, and/or the avoidance of milk and milk products containing the A1 variant of beta-casein, helps increase glutathione levels in the body. Regulation of glutathione levels is beneficial for the management of a number of health problems associated with low levels of antioxidants and elevated oxidative stress.

BACKGROUND OF THE INVENTION

Glutathione (GSH) is an antioxidant involved in several important biochemical pathways. GSH is a thiol peptide formed from three amino acids: glutamic acid, cysteine and glycine. The sulfhydryl group (—SH) of the cysteine residue in GSH provides the critical site for various conjugation and reduction reactions between GSH and other biomolecules. The oxidised dimeric form of GSH (GSSG) can be converted back to GSH through reduction by glutathione reductase. Cysteine availability is a rate-limiting factor for GSH synthesis. The term redox state is often used to describe the balance of GSH and GSSG (and other species) in a biological system such as a cell or organ. An abnormal redox state can develop in a variety of deleterious situations, such as hypoxia, shock and sepsis. Redox mechanisms also control many cellular processes. The primary role of GSH is the prevention of damage to important cellular components caused by reactive oxygen species (ROS). ROS are chemically reactive molecules containing oxygen. Examples include the hydroxyl radical (—OH), superoxide ($O_2^-$), hydrogen peroxide ($H_2O_2$), and peroxynitrite ($ONOO^-$). During times of environmental or physiological stress, ROS levels can increase dramatically. This may result in significant damage to cell structures and is known generally as oxidative stress.

The redox state of a cell may change when the production of ROS or the availability of antioxidants changes. GSH is important in the detoxification and elimination of ROS. A reduction in cellular GSH levels can lead to ROS accumulation and oxidative stress. The regulation of GSH production is essential for cell survival in an oxidative environment.

The condition of oxidative stress is established by an imbalance between the levels or production of ROS and the ability of antioxidant defences to detoxify ROS. There is a need to keep ROS levels within a physiologically safe range and to avoid pathological tissue-damaging levels. Excessive ROS levels lead to oxidative stress which, if not adequately remediated by tissue-repair mechanisms, can cause cell injury or death. Oxidative stress plays a key role in the pathogenesis of many diseases, including cancer, inflammation, kwashiorkor (predominantly protein deficiency), seizure, autism, Down's syndrome, chronic fatigue syndrome, Alzheimer's disease, Parkinson's disease, sickle cell anaemia, liver disease, cystic fibrosis, HIV-AIDS, infection, heart attack, stroke, and diabetes. GSH therefore has an important role in reducing or preventing these diseases and associated symptoms. In addition, GSH is reported to minimise oxidative stress associated with aging, to aid tissue repair following physiological stress resulting from, for example, physical exercise and various sports, and to be beneficial for healthy fertility.

There are numerous examples of antioxidant dietary supplements available in the marketplace. Some are marketed as glutathione supplements. Others are purported to boost GSH levels. Whey protein is known to cause elevated GSH levels, and since bovine milk contains whey protein, milk can also elevate GSH levels. However, the applicant has found that beta-casein proteins, which are also found in bovine milk and the milk of other mammals, and particularly certain types of beta-caseins, are especially effective at maximising GSH levels in blood and tissue relative to other types of beta-caseins.

Milk, mainly bovine milk, consumed in populations throughout the world, is a major source of protein in human diets. Bovine milk typically comprises around 30-35 grams per litre of protein. Caseins make up the largest component (80%) of that protein, and beta-caseins make up about 37% of the caseins. In the past two decades the body of evidence implicating casein proteins, especially beta-caseins, in a number of health disorders has been growing. Beta-caseins can be categorised as A1 type beta-casein or A2 type beta-casein, depending on whether they have a proline or a histidine amino acid at position 67 of the beta-casein amino acid sequence. This difference affects the ability of the beta-casein to produce a specific heptapeptide fragment on enzymatic digestion known as BCM-7. A1 beta-casein and A2 beta-casein are the predominant beta-caseins in milk consumed in most human populations.

The applicant and others have previously determined a link between the consumption of A1 beta-casein in milk and milk products and the incidence of certain health conditions including type I diabetes (WO 1996/014577), coronary heart disease (WO 1996/036239) and neurological disorders (WO 2002/019832). Further, the applicant has shown a link between A1 beta-casein and bowel inflammation (WO 2014/193248), the symptoms of lactose intolerance (WO 2015/005804), and high blood glucose levels (WO 2015/026245).

The applicant has now found conclusive scientific evidence for a direct link between the consumption of A2 beta-casein and elevated GSH levels in blood and tissue. The applicant has therefore found a new way to treat the conditions mentioned above or to manage the symptoms of these conditions.

It is therefore an object of the invention to provide a method for improving the antioxidant capacity in an animal, or to at least provide a useful alternative to existing methods.

SUMMARY OF THE INVENTION

In a first aspect of the invention there is provided a method of improving the antioxidant capacity in an animal by providing to the animal a composition containing beta-casein, where the beta-casein comprises at least 75% by weight of one or more beta-caseins not capable of producing beta-casomorphin-7 on enzymatic digestion.

The one or more beta-caseins are preferably selected from the A2 type beta-caseins.

In certain embodiments of the invention the composition is ingested to increase the level of glutathione in the blood or tissue of the animal.

Further, in certain embodiments, ingestion of the composition avoids or reduces the risk of diseases or disorders associated with oxidative stress. The diseases or disorders associated with oxidative stress may include cancer, inflammation, kwashiorkor (protein deficiency), seizure, autism, Down's syndrome, chronic fatigue syndrome, Alzheimer's disease, Parkinson's disease, sickle cell anaemia, liver disease, cystic fibrosis, HIV, AIDS, infection, heart attack, stroke, and diabetes.

In other embodiments of the invention ingestion of the composition avoids or reduces the effects of aging, promotes the recovery of tissue following physical exercise, or promotes fertility.

In preferred embodiments of the invention the animal is a human. The animal may alternatively be any other animal susceptible to oxidative stress, including for example dogs or cats.

In a second aspect of the invention there is provided a composition for improving the antioxidant capacity in an animal by providing to the animal a composition containing beta-casein, where the beta-casein comprises at least 75% by weight of one or more beta-caseins not capable of producing beta-casomorphin-7 on enzymatic digestion.

In another aspect of the invention there is provided the use of a composition for improving the antioxidant capacity in an animal by providing to the animal a composition containing beta-casein, where the beta-casein comprises at least 75% by weight of one or more beta-caseins not capable of producing beta-casomorphin-7 on enzymatic digestion.

In another aspect of the invention there is provided the use of milk in the manufacture of a composition for improving the antioxidant capacity in an animal, where the milk contains beta-casein and where the beta-casein comprises at least 75% by weight of one or more beta-caseins not capable of producing beta-casomorphin-7 on enzymatic digestion.

In another aspect of the invention there is provided the use of beta-casein in the manufacture of a composition containing beta-casein for improving the antioxidant capacity in an animal, where the beta-casein comprises at least 75% by weight of one or more beta-caseins not capable of producing beta-casomorphin-7 on enzymatic digestion. The beta-casein is preferably a component of milk. The milk is preferably bovine milk.

In another aspect of the invention there is provided the use of a composition containing beta-casein as an antioxidant, where the beta-casein comprises at least 75% by weight of one or more beta-caseins not capable of producing beta-casomorphin-7 on enzymatic digestion.

The amount of the one or more beta-caseins not capable of producing beta-casomorphin-7 on enzymatic digestion may be any amount in the range of 75% to 100% by weight of the beta-casein, for example at least 90%, at least 95%, at least 98%, at least 99%, or even 100%.

In certain embodiments of the invention, the composition is milk or a milk product. The milk may be milk powder or liquid milk. The milk product may be cream, yoghurt, quark, cheese, butter, ice cream, or any other product derived from milk or containing casein or a casein derivative including infant formula, an adult nutritional product, a protein supplement, or a petfood.

In some embodiments of the invention the milk is obtained by genotype testing or phenotype testing of bovine cows, and milking only those cows which have been determined to produce only the A2 type of beta-casein in their milk. A herd of cows may be formed prior to milking comprising only those cows which have been determined to produce only the A2 type of beta-casein in their milk.

DETAILED DESCRIPTION

The invention relates to a composition containing the protein beta-casein and its use for improving antioxidant capacity in animals, especially humans. Importantly, the beta-casein is the A2 variant of beta-casein. The beta-casein in the composition is 100% A2 beta-casein, or makes up at least 75% by weight of the total beta-casein variants present in the composition. The importance of the predominance of the A2 variant in the composition is due to the fact that the applicant has shown that there is a direct link between the consumption of milk containing only the A2 beta-casein variant and elevated levels of GSH and cysteine (a GSH precursor) in rabbits and humans. GSH and cysteine levels were found to be higher when beta-casein in the diet is A2 beta-casein rather than A1 beta-casein.

This has important implications for the prevention, treatment or management of diseases or disorders associated with physiologically high levels of ROS. The antioxidant GSH helps regulate ROS levels. Therefore maximising the levels of GSH in blood and tissue is beneficial for avoiding or reducing the symptoms of a wide variety of diseases including cancer, inflammation, kwashiorkor (protein deficiency), seizure, autism, Down's syndrome, chronic fatigue syndrome, Alzheimer's disease, Parkinson's disease, sickle cell anaemia, liver disease, cystic fibrosis, HIV, AIDS, infection, heart attack, stroke, and diabetes, for aiding tissue repair following physiological stress, for slowing or minimising the effects of the aging process, and for improving fertility.

Since the primary, if not only, source of beta-caseins in the diet of most human populations is milk or products derived from milk, and since most milk consumed contains a mixture of the A1 and A2 variants of beta-casein only (as explained below), the consumption of milk (or products made from such milk) having a high content of the A2 variant will necessarily mean that the consumption of the A1 variant is low. Accordingly, the invention is based on the reduction or elimination of A1 beta-casein in the diet, and the promotion of A2 beta-casein, and this is achieved by ensuring that the beta-casein in beta-casein containing food compositions, especially milk and milk products, is predominantly A2 beta-casein or is preferably exclusively A2 beta-casein.

Ideally, the beta-casein in the composition is 100% A2 beta-casein. The complete elimination of A1 beta-casein therefore maximises the potential to maintain high levels of GSH in blood and tissue, and consequently the avoidance of adverse symptoms and outcomes associated with redox imbalance and excessive levels of ROS. However, the beta-casein in the composition does not need to be 100% A2 beta-casein. The beneficial effects of high GSH levels may be observed in any composition where the beta-casein is predominantly A2 beta-casein, for example, any amount between 75% by weight and 100% by weight, including but not limited to 80%, 90%, 95%, 98% and 99% by weight.

The composition of the invention is typically milk, but may also be any milk product such as cream, yoghurt, quark, cheese, butter, ice cream, or any product containing casein or casein derivatives such as sodium caseinate. Examples of such products include infant formula, adult nutritional products, protein supplements, and petfoods. The composition may also be a non-milk product containing beta-casein that has been obtained from milk. The composition may be beta-casein itself, or may be prepared from beta-casein, which beta-casein may be in solid form such as powder or granules or in the form of a solid cake.

The milk may be in the form of fresh milk, milk powder, liquid milk reconstituted from a powder, skim milk, homogenised milk, condensed milk, evaporated milk, pasteurised milk or non-pasteurised milk, or any other form of milk.

While the milk may be obtained from any mammal, including humans, goats, pigs and buffalo, in preferred embodiments of the invention the milk is bovine milk.

The composition of the invention is intended for consumption by humans primarily, but it should be appreciated that the health benefits are also relevant for some other animals such as cats, dogs and other domestic animals.

Beta-caseins can be categorised generally as the A1 type and the A2 type of beta-casein. A1 beta-casein and A2 beta-casein are the predominant beta-caseins in milk consumed in most human populations. A1 beta-casein differs from A2 beta-casein by a single amino acid. A histidine amino acid is located at position 67 of the 209 amino acid sequence of A1 beta-casein, whereas a proline is located at the same position of A2 beta-casein. This single amino acid difference is, however, critically important to the enzymatic digestion of beta-caseins in the gut. The presence of histidine at position 67 allows a protein fragment comprising seven amino acids, known as beta-casomorphin-7 (BCM-7), to be produced on enzymatic digestion. Thus, BCM-7 is a digestion product of A1 beta-casein. In the case of A2 beta-casein, position 67 is occupied by a proline which hinders cleavage of the amino acid bond at that location. Thus, BCM-7 is not a digestion product of A2 beta-casein.

Other beta-casein variants, such as B beta-casein and C beta-casein, also have histidine at position 67, and other variants, such as A3, D, E and I, have proline at position 67. But these variants are found only in very low levels, or not found at all, in milk from cows of European origin. Thus, in the context of this invention, the term A1 beta-casein refers to any beta-casein having histidine at position 67 and thus the ability to produce BCM-7 on enzymatic digestion, and the term A2 beta-casein refers to any beta-casein having proline at position 67 and thus having no ability to produce BCM-7 on enzymatic digestion.

The milk of cows can be tested for the relative proportions of A1 type beta-caseins and A2 type beta-caseins. Alternatively, cows can be genetically tested for their ability to produce milk containing A1 type beta-caseins or A2 type beta-caseins or a combination of both. These methods and techniques are well-known.

The intracellular concentration of GSH in most cells averages 1-2 mM, and may vary from about 10 mM in hepatocytes to 0.2 mM in neurons. Hepatocytes provide much of the GSH found in plasma. Because of the relatively low content of GSH in neurons, replenishment of GSH by the reduction of GSSG becomes an especially important process in neurons. GSH can be transported out of cells and in blood using a carrier-dependent facilitated mechanism. Some dietary and intestinally derived GSH can also enter the portal venous plasma. The liver is the main source of plasma GSH, where GSH is synthesised from cysteine. The brain, kidneys, lungs, and intestines are major consumers of liver-derived GSH. The inter-organ metabolism of GSH enables the transport of cysteine and cystine in a nontoxic form between tissues, and also helps to maintain intracellular GSH concentrations and an optimal redox state. A sub-physiological level of GSH can lead to accumulation of ROS and consequently oxidative stress. Conversely, increased GSH synthesis increases antioxidant potential and promotes metabolic activity.

Cells suffer from oxidative stress usually because of one of three factors: 1) an increase in oxidant generation, 2) a decrease in antioxidant protection, and 3) a failure to repair oxidative damage. Oxidative damage can occur in DNA, proteins and lipids. GSH plays a central role in neutralising almost all ROS reactions via direct and indirect pathways. The main cellular damage caused by ROS is the oxidation of macromolecules, such as polyunsaturated fatty acids in membrane lipids, essential proteins, and DNA.

Support for the invention may be found in the experiments described in the Examples.

Figure 1:
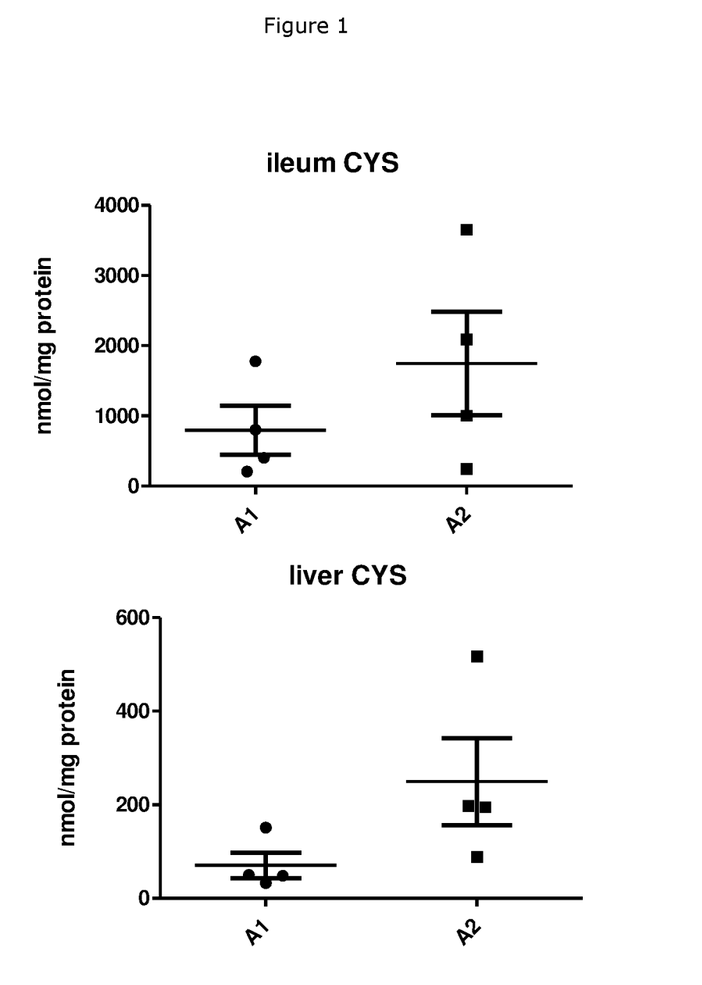
FIG. 1 shows the levels of cysteine in the ileum and liver of rabbits fed A1 beta-casein and A2 beta-casein diets.
Figure 2:
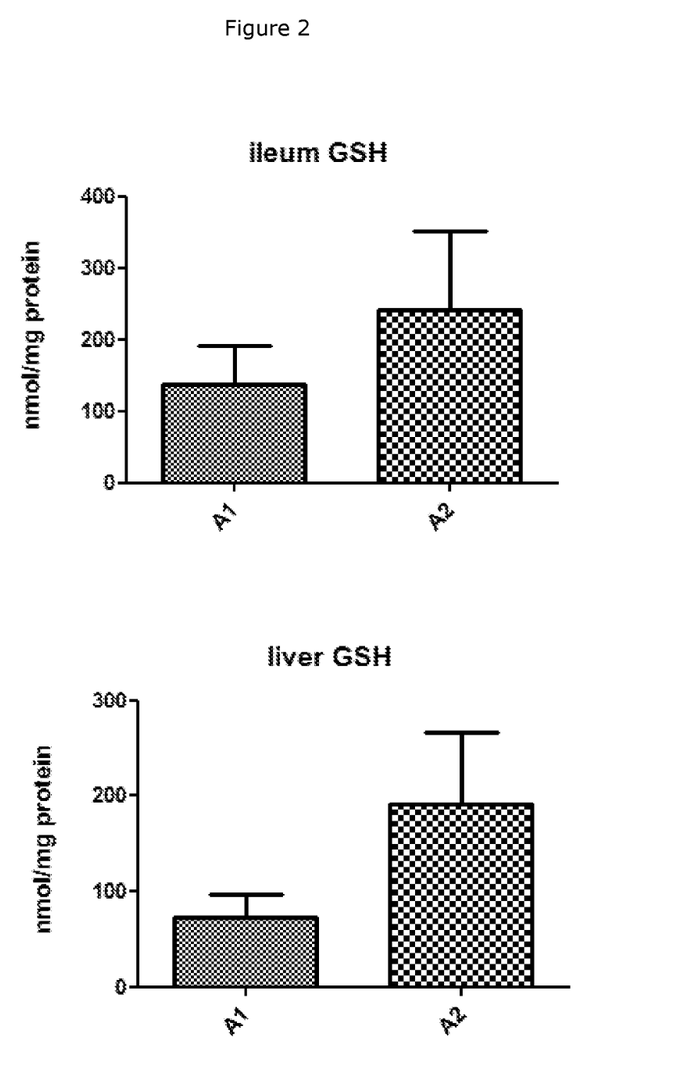
FIG. 2 shows the levels of GSH in the ileum and liver of rabbits fed A1 beta-casein and A2 beta-casein diets.
Figure 3:
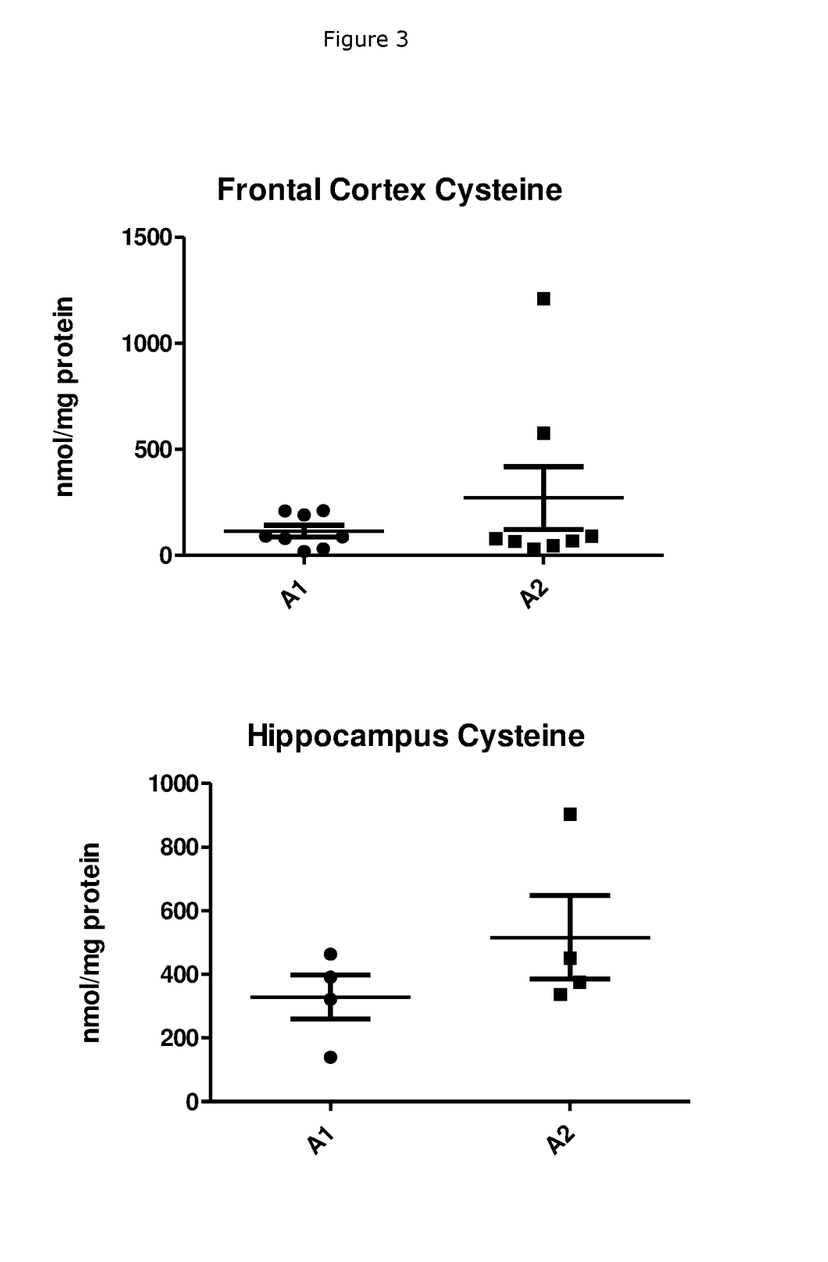
FIG. 3 shows the levels of cysteine in the frontal cortex and hippocampus of rabbits fed A1 beta-casein and A2 beta-casein diets.
Figure 4:
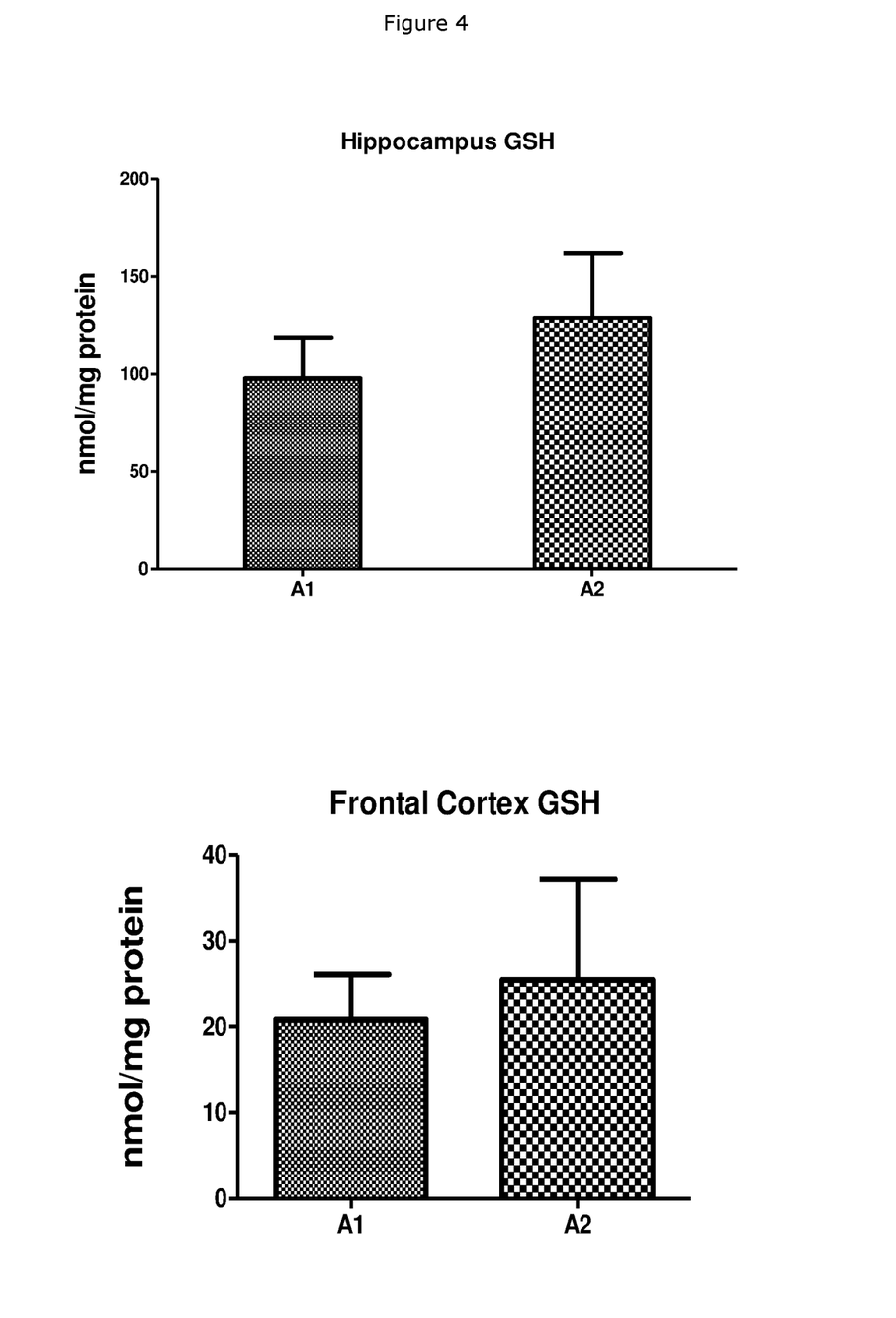
FIG. 4 shows the levels of GSH in the frontal cortex and hippocampus of rabbits fed A1 beta-casein and A2 beta-casein diets.

Example 1 is a study of rabbits fed skimmed milk powder diets. The skimmed milk powder used was derived from either milk containing only the A1 variant of beta-casein (A1) or milk containing only the A2 variant of beta-casein (A2). The results are depicted in FIGS. 1 to 4. FIGS. 1 and 2 show an increased uptake of both cysteine and GSH in the ileum and in the liver for A2-fed rabbits. Since the liver is the main storage organ for GSH homeostasis, an increase in liver GSH indicates an overall increase in GSH levels in the body. The frontal cortex and hippocampus regions from the brain isolated from rabbits fed the A2 diet also had elevated GSH levels compared to the same brain regions isolated from rabbits on the A1 diet. Low levels of GSH in the frontal cortex have been implicated in disorders such as autism, ADHD, Down's syndrome and schizophrenia. Low levels in the hippocampus may affect memory recovery. Low levels of cysteine in the hippocampus have been found in patients suffering from autism and Alzheimer's disease. The findings indicate that A2-fed rabbits had a relatively higher antioxidant capacity through various body organs and especially in the brain compared with A1-fed rabbits.

Example 2 describes a double-blind, randomised, controlled, 2×2 cross-over study in which healthy participants consumed 2×250 ml of conventional milk containing both the A1 and A2 beta-casein variants, or milk containing only the A2 beta-casein variant, each day. Plasma glutathione concentrations were measured. The consumption of milk containing only A2 beta-casein was found to be associated with a greater increase in plasma glutathione concentration compared with milk containing both beta-casein variants.

Prior studies showed that whey protein, which does not yield BCM-7 during proteolysis, promotes cysteine absorption and the synthesis of GSH, whereas opioid peptides derived from beta-casein and wheat inhibit cysteine uptake, decrease GSH concentrations, and decrease the anti-oxidant potential (i.e. decrease the GSH/GSSG ratio). The results of Example 2 are consistent with the results of these prior studies, and indicate that A1 beta-casein limits the amount of cysteine that is absorbed from milk, and hence the capacity to synthesise GSH. Eliminating A1 beta-casein from the milk diet allowed for greater increases in GSH synthesis, possibly via eliminating the inhibitory effects of BCM-7 on cysteine uptake. Thus, the daily consumption of conventional commercially available milk is associated with an increase in GSH levels, possibly as a consequence of increased supply of cysteine in whey protein. However, the magnitude of elevated antioxidant is higher when consuming milk containing only the A2 variant of beta-casein compared to milk containing both A1 and A2 beta casein together. These results imply that eliminating A1 beta-casein from milk may allow for greater increases in GSH levels, and hence greater antioxidant capacity.

The experiments described above all show a clear link between the consumption of A2 beta-casein and high levels of GSH (and its precursor cysteine) in the blood as well as liver and brain tissue compared with the consumption of A1 beta-casein. Since GSH is the body's primary defence against ROS, and ROS are known to be strongly implicated in a wide variety of diseases, the therapeutic and preventative benefits of replacing dietary A1 beta-casein with A2 beta-casein are clear.

The present invention provides a solution that is comparatively easy to manage, i.e. by avoiding milk or milk products that contain A1 beta-casein and ensuring that milk and milk products in the diet contain beta-casein that is predominantly A2 beta-casein, preferably 100% A2 beta-casein.

Any reference to prior art documents in this specification is not to be considered an admission that such prior art is widely known or forms part of the common general knowledge in the field.

As used in this specification, the words "comprises", "comprising", and similar words, are not to be interpreted in an exclusive or exhaustive sense. In other words, they are intended to mean "including, but not limited to".

The invention is further described with reference to the following examples. It will be appreciated that the invention as claimed is not intended to be limited in any way by these examples.

EXAMPLES

Example 1: Effect of Beta-Casein A1 v. Beta-Casein A2 Consumption on Cysteine and GSH Levels in Rabbits A total of 10 male rabbits (NZW, age- and/or weight-matched) were randomly divided into two groups and placed on rabbit feeds made with skimmed milk powder (SMP) as the main protein source for a total of 12 weeks. The total protein content was 16.8% with 60% of the protein originating from SMP, i.e. 10% of the diet consisted of milk protein. The SMP used was derived from either milk containing only the A1 variant of beta-casein (A1) or milk containing only the A2 variant of beta-casein (A2). The SMP diet was tested for palatability to prevent any issues relating to the rabbits refusing to consume the feed. At the end of the 12 week period, the rabbits were euthanised. Tissues samples were procured and stored at −80° C. until further use. The tissues were lysed using lysis buffer 1× and tissue lysates were sonicated for 15 seconds on ice. 100 µL of the sonicate was used to determine protein content. The remaining lysate was added to a microcentrifuge tube and an equal volume of 0.4N perchloric acid was added, followed by incubation on ice for 5 min. Samples were centrifuged at 13,000 RPM and the supernatant transferred to new microcentrifuge tubes. 100 µL of sample was added to a conical micro-autosampler vial and kept at 4° C. in the autosampler cooling tray. 10 µL of this sample was injected into the HPLC system. The separation of redox and methylation pathway metabolites was accomplished using an Agilent Eclipse XDB-C8 analytical column (3×150 mm; 3.5 µm) and an Agilent Eclipse XDB-C8 (4.6×12.5 mm; 5 µm) guard column. Two mobile phases were used. Mobile Phase A was 0% acetonitrile, 25 mM sodium phosphate, 1.4 mM 1-octanesulfonic acid, adjusted to pH 2.65 with phosphoric acid. Mobile Phase B was 50% acetonitrile. The flow rate was initially set at 0.6 mL/min and a step gradient was utilized: 0-9 min 0% B, 9-19 min 50% B, 19-30 min 50% B. The column was then equilibrated with 5% B for 12 min prior to the next run. Temperature was maintained at 27° C. The electrochemical detector wan an ESA CoulArray with BDD Analytical cell Model 5040 and the operating potential was set at 1500 mV. Sample concentrations were determined from the peak areas of metabolites using standard calibration curves and ESA-supplied HPLC software. Sample concentrations were normalised against protein content. In some cases samples were diluted in mobile phase as needed or up to 50 µL of sample was injected to ensure that thiol levels were within the range of the standard curve.

The target tissues including GI tract, liver, and two different parts of the brain (hippocampus and frontal cortex) were collected and analysed for cysteine levels and GSH levels. The results are shown in FIGS. 1 to 4.

Example 2: Effect of Beta-Casein A1 V. Beta-Casein A2 on GSH Concentrations in Plasma Samples in Humans Eligible Chinese males or females included those aged 25-68 years who irregularly consumed milk and had self-reported intolerance to commercial milk, self-reported mild to moderate digestive discomfort after milk consumption, and had normal electrocardiograms and blood pressure during quiet respiration. A total of 21 males and 24 females with a mean±standard deviation (SD) age of 46.6±14.0 years were enrolled. Twenty-three had confirmed lactose deficiency based on the results of urinary galactose tests.

The participants consumed commercially available conventional milk containing the A1 and A2 variants of beta-casein (A1/A2) in phase 1 or commercially available milk containing only the A2 variant of beta-casein (A2) in phase 2 (A1/A2→A2; sequence 1), or vice versa (A2→A1/A2; sequence 2). The ratio of A1 to A2 beta-casein in milk containing both variants of beta-casein was determined to be 42:58 by UPLC-DAD and tandom mas spectrometry. Each study phase lasted 2 weeks with 2-week washout periods before entering phase 1 and between phases 1 and 2. The participants were instructed to consume 250 ml of milk after 2 meals per day, every day. They were prohibited from consuming other dairy products, but could consume non-dairy milk products during the study. The study was conducted in accordance with the Declaration of Helsinki as amended in Seoul 2008 and was approved by the ethics committee of the Shanghai Nutrition Society (approval number: SNSIRB #2014[002]). The study was registered with ClinicalTrials.gov (identifier: NCT02406469).

Blood samples were collected at baseline and at the end of each study phase for measurement of laboratory variables, including GSH. Plasma was stored at −80° C. until required for assays. The plasma samples were thawed in ice and 5 μL of a 0.4 N perchloric acid solution was added to 200 μL of plasma to precipitate any remaining proteins.

Total GSH levels were measured at 412 nm, using the recycling reaction of GSH with dithionitrobenzoate in the presence of excess GSH reductase. The results were expressed as nmol of 5-thio-2-nitrobenzoic acid formed (expressed as $min^{-1}$ $mg^{-1}$ protein). The GSH concentration was measured twice for each sample in independent assays.

The GSH concentrations were highly skewed based on the Kolmogorov-Smirnov test. Therefore, the data were analysed using the Wilcoxon two-sample test with phase and cross-over as fixed effects, and $P<0.05$ was taken to indicate a statistically significant phase or cross-over effect.

Figure 5:
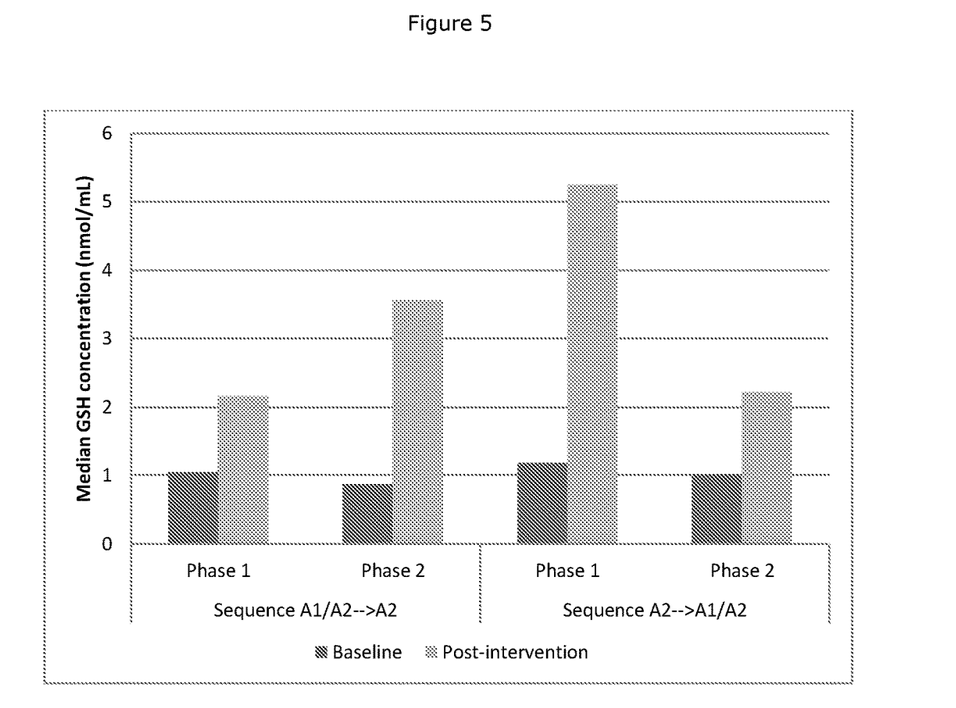
FIG. 5 shows median GSH concentrations in humans before and after consumption of milk containing either only A2 beta-casein or both A1 beta-casein and A2 beta-casein.

The median GSH concentrations dataset measured at the start and end of each study phase in both sequences are depicted in FIG. 5. The results of the Wilcoxon two-sample test are shown in Table 1.

TABLE 1

Wilcoxon two-sample test for plasma glutathione concentrations

|  |  | Sequence | N | Wilcoxon rank sum | Expected under H0 | Standard deviation under H0 | Mean score | P-value |
|---|---|---|---|---|---|---|---|---|
| First measure | Phase | A1/A2→A2 | 22 | 386.5 | 506 | 44.0402 | 17.57 | 0.0059 |
|  |  | A2→A1/A2 | 23 | 648.5 | 529 | 44.0402 | 28.20 |  |
|  | Cross-over | A1/A2→A2 | 22 | 520.0 | 506 | 44.0416 | 23.64 | 0.7615 |
|  |  | A2→A1/A2 | 23 | 525.0 | 529 | 44.0416 | 22.39 |  |
| Second measure | Phase | A1/A2→A2 | 22 | 386.0 | 506 | 44.0416 | 17.55 | 0.0058 |
|  |  | A2→A1/A2 | 23 | 649.0 | 529 | 44.0416 | 28.22 |  |
|  | Cross-over | A1/A2→A2 | 22 | 517.0 | 506 | 44.0416 | 23.50 | 0.8134 |
|  |  | A2→A1/A2 | 23 | 518.0 | 529 | 44.0416 | 22.52 |  |

Consumption of milk containing only the A2 beta-casein variant was associated with significantly greater increases in plasma GSH concentrations from baseline to the end of the study phase compared with the consumption of milk containing both beta-casein variants. This increase occurred in both sequences irrespective of which milk product was consumed first. The mean±SEM change in GSH concentrations from baseline was 4.01±0.61 nmol/mL for milk containing A2 beta-casein compared with 1.99±0.50 nmol/mL for milk containing both A1 beta-casein and A2 beta-casein. The change from baseline GSH levels with A2 beta-casein tended to be greater in phase 1 (Sequence A2→A1/A2) than in phase 2 (Sequence A1/A2→A2) (4.07 vs. 2.70 nmol/mL).

Although the invention has been described by way of example, it should be appreciated that variations and modifications may be made without departing from the scope of the invention as defined in the claims. Furthermore, where known equivalents exist to specific features, such equivalents are incorporated as if specifically referred in this specification.

The invention claimed is:

1. A method of improving antioxidant capacity in a human by increasing the level of glutathione in the blood or tissue of the human, the method comprising providing to the human a composition containing bovine beta-casein in an amount effective to increase the level of glutathione in the blood or tissue of the human, where the beta-casein comprises at least 75% by weight of one or more beta-caseins selected from the A2 type beta-caseins.

2. The method as claimed in claim 1 where ingestion of the composition avoids or reduces the risk of one or more diseases or disorders associated with oxidative stress.

3. The method as claimed in claim 2 where the one or more diseases or disorders associated with oxidative stress are selected from the group consisting of cancer, inflammation, kwashiorkor (protein deficiency), seizure, autism, Down's syndrome, chronic fatigue syndrome, Alzheimer's disease, Parkinson's disease, sickle cell anaemia, liver disease, cystic fibrosis, HIV, AIDS, infection, heart attack, stroke, and diabetes.

4. The method as claimed in claim 1 where ingestion of the composition avoids or reduces the effects of aging, promotes the recovery of tissue following physical exercise, or promotes fertility.

5. The method as claimed in claim 1 wherein the beta-casein comprises at least 90% by weight A2 beta-casein.

6. The method as claimed in claim 1 wherein the beta-casein comprises 100% A2 beta-casein.

7. The method as claimed in claim 1 wherein the composition is milk or a milk product.

8. The method as claimed in claim 7 wherein the milk is fresh milk, milk powder, liquid milk reconstituted from powder, skim milk, homogenised milk, condensed milk, evaporated milk, pasteurised milk, or non-pasteurised milk.

9. The method as claimed in claim 7 wherein the milk product is cream, yoghurt, quark, cheese, butter, ice cream, infant formula, an adult nutritional product, a protein supplement, or a pet food.

10. The method as claimed in claim 7 wherein the milk is obtained by genotype testing or phenotype testing of bovine cows, and milking only those cows which have been determined to produce only the A2 type of beta-casein in their milk.

11. The method as claimed in claim 10 wherein a herd of cows is formed comprising only those cows which have been determined to produce only the A2 type of beta-casein A2 in their milk and then milking one or more cows of the herd.

12. The method as claimed in claim 6 where ingestion of the composition avoids or reduces the risk of one or more diseases or disorders associated with oxidative stress.

13. The method as claimed in claim 12 where the one or more diseases or disorders associated with oxidative stress are selected from the group consisting of cancer, inflammation, kwashiorkor (protein deficiency), seizure, autism, Down's syndrome, chronic fatigue syndrome, Alzheimer's disease, Parkinson's disease, sickle cell anaemia, liver disease, cystic fibrosis, HIV, AIDS, infection, heart attack, stroke, and diabetes.

14. The method as claimed in claim 6 where ingestion of the composition avoids or reduces the effects of aging, promotes the recovery of tissue following physical exercise, or promotes fertility.

15. The method as claimed in claim 6 wherein the composition is milk or a milk product.

\* \* \* \* \*